(12) United States Patent
Gurjar et al.

(10) Patent No.: US 10,508,075 B2
(45) Date of Patent: Dec. 17, 2019

(54) PROCESS FOR PREPARATION OF TRIENTINE DIHYDROCHLORIDE

(71) Applicant: EMCURE PHARMACEUTICALS LIMITED, Pune (IN)

(72) Inventors: Mukund Gurjar, Pune (IN); Shashikant Joshi, Pune (IN); Devising Pardeshi, Pune (IN); Mangesh Kamble, Pune (IN); Lakindrasing Girase, Pune (IN); Samit Mehta, Pune (IN)

(*) Notice: Subject to any disclaimer, the term of this patent is extended or adjusted under 35 U.S.C. 154(b) by 0 days.

(21) Appl. No.: 15/760,239

(22) PCT Filed: Sep. 13, 2016

(86) PCT No.: PCT/IB2016/055439
§ 371 (c)(1),
(2) Date: Mar. 15, 2018

(87) PCT Pub. No.: WO2017/046695
PCT Pub. Date: Mar. 23, 2017

(65) Prior Publication Data
US 2018/0265451 A1 Sep. 20, 2018

(30) Foreign Application Priority Data
Sep. 18, 2015 (IN) .......... 3560/MUM/2015

(51) Int. Cl.
*C07C 209/50* (2006.01)
(52) U.S. Cl.
CPC .................. *C07C 209/50* (2013.01)
(58) Field of Classification Search
None
See application file for complete search history.

(56) References Cited

U.S. PATENT DOCUMENTS

2006/0041170 A1* 2/2006 Jonas .................... C07C 255/30
564/463

FOREIGN PATENT DOCUMENTS

| CN | 102924289 A | 2/2013 |
| JP | 2010105943 A | 5/2010 |
| KR | 2008/0022940 A | 3/2008 |
| WO | WO2006027705 A2 | 3/2016 |

OTHER PUBLICATIONS

International Search Report and Written Opinion for International Application No. PCT/IB2016/055439, dated Dec. 1, 2016, 2 pages.
"Process for preparation of Trientine hydrochloride", IP.com Journal, vol. 16 No. 1A, Dec. 23, 2015, 5 Pages.
Rupert Purchase, "The purification of triethylenetetramine ar dihydrochloride for the treatment of Wilson's disease", Journal Chemical Research, vol. 2005, No. 4, Apr. 1, 2005, pp. 233-235, GB ISSN: 1747-5198.
Extended European Search Report issued in EP Application No. 16845804, dated Mar. 28, 2019, 11 pages.

* cited by examiner

*Primary Examiner* — Sudhakar Katakam
*Assistant Examiner* — Jennifer C Sawyer
(74) *Attorney, Agent, or Firm* — Dave Law Group LLC; Raj S. Dave

(57) ABSTRACT

The present invention provides a process for preparation of trientine dihydrochloride (1) comprising reaction of protected triethylene tetramine with hydrochloric acid in an aqueous system to yield the dihydrochloride salt wherein the formation of inorganic impurities and undesired salts is controlled significantly.

5 Claims, No Drawings

PROCESS FOR PREPARATION OF TRIENTINE DIHYDROCHLORIDE

CROSS REFERENCE TO RELATED APPLICATION(S)

This application is the U.S. national stage application under 35 U.S.C. § 371 of International Patent Application No. PCT/IB2016/055439, filed on Sep. 13, 2016, claims the benefit of priority under 35 U.S.C. § 119 of India Patent Application No. 3560/MUM/2015, filed on Sep. 18, 2015, the contents of each which are hereby incorporated by reference in their entireties.

FIELD OF THE INVENTION

The present invention relates to a process for the preparation of trientine hydrochloride having desired purity. Specifically, the invention relates to a process for preparation of trientine dihydrochloride (1) comprising the reaction of protected triethylenetetramine with hydrochloric acid in an aqueous medium to directly yield the corresponding dihydrochloride salt having desired purity.

BACKGROUND OF THE INVENTION

Trientine, chemically known as triethylenetetramine or N,N'-bis(2-aminoethyl)-1,2-ethanediamine belongs to the class of polyethylene polyamines. Trientine dihydrochloride is a chelating agent which is used to bind and remove copper in the body in the treatment of Wilson's disease.

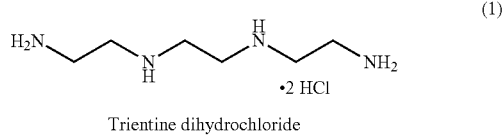

Trientine dihydrochloride (1)

Trientine dihydrochloride formulation, developed by Aton with the proprietary name SYPRINE, was approved by USFDA on Nov. 8, 1985 for the treatment of patients with Wilson's disease, who are intolerant to penicillamine. Trientine dihydrochloride, due to its activity on copper homeostasis, is being studied for various potential applications in the treatment of internal organs damage in diabetics, Alzheimer's disease and cancer.

Various synthetic methods for preparation of triethylenetetramine (TETA) and the corresponding dihydrochloride salt have been disclosed in the prior art.

U.S. Pat. No. 4,806,517 discloses the synthesis of triethylenetetramine from ethylenediamine and monoethanolamine using Titania supported phosphorous catalyst while U.S. Pat. Nos. 4,550,209 and 5,225,599 disclose catalytic condensation of ethylenediamine and ethylene glycol for the synthesis of linear triethylenetetramine using catalysts like zirconium trimethylene diphosphonate, or metatungstate composites of titanium dioxide and zirconium dioxide.

U.S. Pat. No. 4,503,253 discloses the preparation of triethylenetetramine by reaction of an alkanolamine compound with ammonia and an alkyleneamine having two primary amino groups in the presence of a catalyst, such as supported phosphoric acid wherein the support is comprised of silica, alumina or carbon.

The methods described above for preparation of triethylenetetramine require high temperatures and pressure. Further, due to the various possible side reactions and consequent associated impurities, it is difficult to control the purity of the desired amine.

CN 102924289 discloses a process for trientine dihydrochloride comprising reduction of N,N'-dibenzyl-,N,N'-bis[2-(1,3-dioxo-2H-isoindolyl)ethyl]ethanediamine using hydrazine hydrate to give N,N'-dibenzyl-,N,N'-bis(2-aminoethyl)ethanediamine, which, upon condensation with benzyl chloroformate gave N,N'-dibenzyl-,N,N'-bis[2-(Cbz-amino)ethyl]ethanediamine, and further reductive deprotection to give the desired compound.

CS 197,093 discloses a process comprising reaction of triethylenetetramine with concentrated hydrochloric acid to obtain the crystalline tetrahydrochloride salt. Further reaction of the salt with sodium ethoxide in solvent ethanol, filtration of the solid sodium chloride which is generated in the process, followed by slow cooling and crystallization of the filtrate provided the dihydrochloride salt. Optionally, aqueous solution of the tetrahydrochloride salt was passed through a column of an anion exchanger and the eluate containing free base was treated with a calculated amount of the tetrahydrochloride, evaporated, and the residue was crystallized from aqueous ethanol to yield the dihydrochloride salt.

The process is quite circuitous and cumbersome, requiring use of strong bases, filtration of sodium chloride and results in yields as low as 60%.

U.S. Pat. No. 8,394,992 discloses a method for preparation of triethylenetetramine dihydrochloride wherein tertiary butoxycarbonyl (boc) protected triethylenetetramine is first converted to its tetrahydrochloride salt using large excess of hydrochloric acid in solvent isopropanol, followed by treatment of the resulting tetrahydrochloride salt with a strong base like sodium alkoxide to produce the amine free base (TETA) and sodium chloride salt in anhydrous conditions. The free amine is extracted with tertiary butyl methyl ether (TBME), followed by removal of sodium chloride salt and finally the amine free base TETA is treated with hydrochloric acid in solvent ethanol to give trientine hydrochloride salt.

The method suffers from the following drawbacks.

a) Lengthy process comprising treatment of tetrahydrochloride salt with a base in anhydrous conditions to obtain the amine and its further conversion to TETA dihydrochloride, which includes a number of unit operations such as solvent extraction, washing of filtered solid, solvent concentration, crystallization at various stages of synthesis etc.

b) Use of excessive amounts of hydrochloric acid as well as anhydrous alcoholic and ether solvents.

c) Stringent requirement of complete removal of sodium chloride formed during the process. If the salt is not scrupulously removed, the final product, trientine hydrochloride salt is unlikely to pass the sulphated ash test, which is indicative of complete removal of inorganic impurities from the drug product.

Thus it would be evident that there still exists a need for a convenient, cost effective, and industrially viable process for synthesis of triethylenetetramine dihydrochloride (1) which avoids the following.
a) lengthy synthetic routes for protection and deprotection of the reactant amines and intermediates,
b) excessive use of organic solvents,
c) use of mineral acids in multiple steps The process further eliminates use of strong bases, as well as controls the number of unit operations, and yet provides the desired dihydrochloride in substantially pure form in good yield.

The present inventors have developed a novel process for synthesis of triethylenetetramine dihydrochloride (1) comprising a single step of treating Boc-protected amine (6) with hydrochloric acid to give the desired dihydrochloride salt (1) in substantially pure form and in good yield.

In this way, the present inventors have developed a convenient and cost-effective process by skillfully manipulating the deprotection, salt formation and isolation steps in the synthesis of desired dihydrochloride (1). The method avoids lengthy synthetic steps, strong bases, excessive use of organic solvents, use of multi-molar equivalents of mineral acid and most significantly eliminates the possibility of traces of inorganic salts in the final product. The use of hydrochloric acid in sub-equimolar quantities for simultaneous deprotection and salt preparation reaction results in selective formation of the dihydrochloride salt.

Object of the Invention

An objective of the present invention is to provide triethylenetetramine dihydrochloride of formula (1) having desired purity by a convenient and economical process which does not involve excessive quantities of organic solvents and hydrochloric acid.

Another object of the present invention is to provide an efficient process for preparation of triethylenetetramine dihydrochloride (1), wherein Boc-protected triethylenetetramine (6) is treated with sub-equimolar quantities of hydrochloric acid in aqueous system to provide the dihydrochloride salt directly in a single step.

SUMMARY OF THE INVENTION

The present invention relates to a method for synthesis of triethylenetetramine dihydrochloride of formula (1) in substantially pure form.

An aspect of the invention relates to the reaction of tert-butyl N-(2-aminoethyl)-N-2-[(2-aminoethyl)(tert-butoxy)carbonyl]amino]ethyl}carbamate of formula (6) with hydrochloric acid in aqueous system in the temperature range of 80-110° C. to give triethylenetetramine dihydrochloride (1).

The objectives of the present invention will become more apparent from the following detailed description.

DETAILED DESCRIPTION OF THE INVENTION

The present inventors, in their pursuit for developing a convenient, commercially viable and economical process for obtaining trientine dihydrochloride conforming to regulatory specifications, carried out extensive experimentation aimed at minimizing the synthetic steps as against the circuitous routes disclosed in prior art. Surprisingly, it was observed that a direct, single-step process for preparation of the dihydrochloride salt was possible when the reaction of tertiary butoxycarbonyl protected amine (6) with hydrochloric acid was carried out in an aqueous system at 80 to 110° C. in the pH range of 7-8. In this reaction, hydrochloric acid which was used in less than molar equivalent quantities with respect to the protected amine reactant, served the dual purpose of deprotection of the protecting group and formation of the salt, providing the selective dihydrochloride formation. It was also observed that the reaction could be carried out either at mild pressure in an autoclave or at atmospheric pressure.

This novel strategy thus avoids lengthy, time consuming reaction sequence of preparing tetrahydrochloride salt from the protected diamine, its conversion to trientine free base, followed by re-conversion to the dihydrochloride salt by reaction with hydrochloric acid. Consequently, use of multi-molar equivalents of hydrochloric acid, excessive organic solvents and the multiple unit operations at intermediate stages are avoided to give a convenient and robust process for the dihydrochloride salt (1) which conforms to regulatory requirements.

A noteworthy part of the embodied method was that there was no formation of sodium chloride during the process, due to which the unit operations for separation and filtration of the salt were eliminated and more importantly, problems associated with sulphated ash content, which hampered the purity of the final product; dihydrochloride salt were avoided.

Scheme 1: Method embodied in the present invention for the preparation of triethylenetetramine dihydrochloride (1)

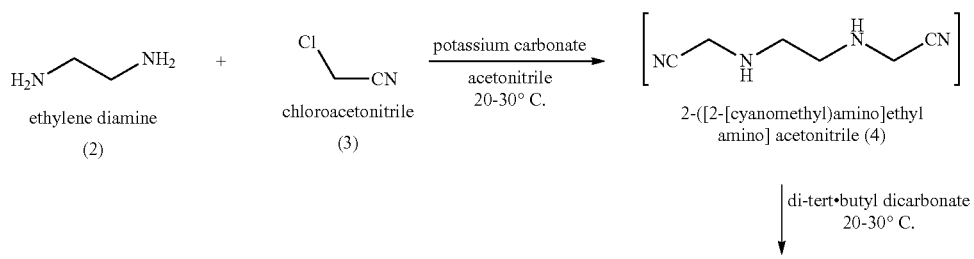

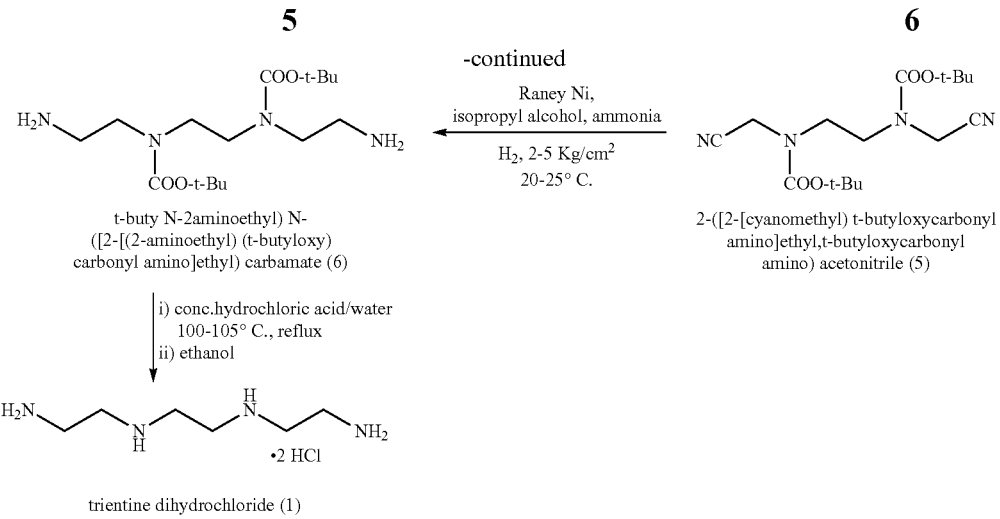

In an embodiment, tert-butyl-N-(2-aminoethyl)-N-2-[(2-aminoethyl)-(tert-butoxy)carbonyl]amino]ethyl}carbamate of formula (6) was treated with concentrated hydrochloric acid.

The amount of hydrochloric acid employed for deprotection of the amine group and subsequent dihydrochloride formation was in the range of 1.6 to 2.1 equivalents with respect to the tertiary butoxycarbonyl-protected diamine (6).

It was noted that if, during the reaction eventually the pH was excessively higher or lower than the range of 7 to 8, there were problems in isolating the desired dihydrochloride salt resulting in substantial yield loss.

The reaction mixture was heated in the temperature range of 80-110° C.

The reaction was carried out at atmospheric pressure or in a pressure vessel (autoclave) wherein the pressure was maintained in the range of 2-10 Kg/cm$^2$.

After completion of the reaction as monitored by TLC, the aqueous reaction mixture was concentrated and ethanol was added to the residue. The resultant mixture was heated till a clear solution was obtained. Further cooling of the reaction mixture, filtration and drying yielded the desired compound, triethylenetetramine dihydrochloride (1) with yield around 80% and purity≥98% (purity within USP limits).

Compound (6) was prepared following known methods by reaction of ethylene diamine (2) with chloroacetonitrile (3) using potassium carbonate as base and solvent acetonitrile to give 2-({2-[(cyanomethyl)amino]ethyl}amino) acetonitrile (4). Compound (4) was further treated with ditertiarybutyl dicarbonate and the resulting boc-protected dinitrile (5) was hydrogenated using Raney nickel, ammonia and isopropyl alcohol to yield compound (6).

Alternatively, the preparation of compound (4) and its further reaction with ditertiarybutyl dicarbonate was carried out in-situ.

The following examples are meant to be illustrative of the present invention. These examples exemplify the invention and are not to be construed as limiting the scope of the invention.

EXAMPLES

Example 1: Preparation of 2-([2-[cyanomethyl]-t-butyloxycarbonylamino]ethyl-t-butyloxy carbonylamino)acetonitrile (5)

Potassium carbonate (481.9 g) was added to a stirred mixture of ethylenediamine (100.0 g) in acetonitrile (800 ml) and cooled to around 10° C. Chloroacetonitrile (263.8 g) was gradually added at same temperature and stirred at 25-30° C., till completion of the reaction, as monitored by HPLC. The mixture was cooled to 5-15° C. and Boc-anhydride (762.1 g) was added to it, followed by stirring at the same temperature. The temperature was raised to 25-30° C. and the mass was stirred till completion of the reaction, as monitored by HPLC.

The reaction mass was filtered and the filtrate was concentrated. Toluene was added to the residue, and the mixture was heated to around 70° C. followed by cooling and filtration to give 2-([2-[(cyanomethyl)-t-butyloxycarbonylamino]ethyl-t-butyloxycarbonylamino) acetonitrile (5).

Yield: 506.8 g
% Yield: 89.9%

Example 2: Preparation of t-butyl(N-2-aminoethyl) N-([2-[(2-aminoethyl)t-butyloxy)carbonylamino]ethyl) carbamate (6)

Raney nickel (120.0 g) in isopropanol (100 ml) was charged into an autoclave, followed by a mixture of Compound 5 (200 g) in isopropanol (400 ml). Cooled ammonia solution prepared by purging ammonia gas in 1400 ml isopropanol, equivalent to 125 g ammonia was gradually charged to the autoclave and the reaction was carried out around 15-25° C. under hydrogen pressure of 2-5 Kg/cm$^2$.

After completion of the reaction, as monitored by HPLC, the mass was filtered, concentrated, and methyl tertiary butyl ether was added to the residue. The mixture was heated to around 50° C., followed by cooling of the mass, stirring, optional seeding with compound 6 and filtration to give tertiary butyl-(N-2-aminoethyl)N-([2-[(2-aminoethyl)-(tert-butyloxy) carbonylamino]ethyl) carbamate.

Yield: 174 g
% Yield: 85%

Example 3: Preparation of Triethylenetetramine Dihydrochloride (1)

Concentrated hydrochloric acid (121.5 g) was gradually added to a stirred mixture of tertiary-butyl-N-(2-aminoethyl)-N-2-[(2-aminoethyl)-(tert-butoxy) carbonyl]amino] ethyl}carbamate (Compound 6, 200.0 g) and water (1400 ml) at 20-30° C. The reaction mixture was heated in the temperature range of 100-105° C. till completion of the reaction, as monitored by HPLC, with optionally distilling out water, if so required.

The reaction mass was concentrated and ethanol (600 ml) was added to the residue, followed by heating till a clear solution was obtained. The reaction mixture was gradually cooled with stirring, filtered and dried to provide triethylenetetramine dihydrochloride (1).

Yield: 88.9 g, (70%)
Purity: ≥99%

The invention claimed is:

1. A process comprising preparing Trientine dihydrochloride directly and selectively in a single step reaction consisting of reacting a compound of Formula (6) with 1.6 to 2.1 molar equivalents of hydrochloric acid in an aqueous medium to produce the Trientine dihydrochloride without formation of Trientine tetrahydrochloride

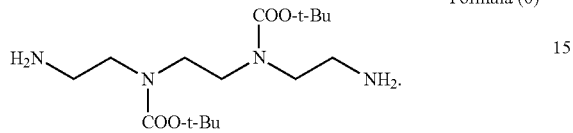

Formula (6)

2. The process as claimed in claim 1, wherein the reaction temperature is maintained in the range of 80 to 110° C.

3. The process as claimed in claim 1, wherein the reaction mass obtained after completion of the reaction is concentrated, treated with ethanol, cooled and filtered to yield the Trientine dihydrochloride.

4. The process as claimed in claim 1, wherein the reaction is carried out at 80 to 110° C. in an autoclave or at atmospheric pressure.

5. The process of claim 1, wherein the Trientine tetrahydrochloride is subsequently converted to trientine free base and sodium chloride in presence of a strong base and an organic solvent.

* * * * *